United States Patent
Asmussen et al.

[19]

[11] Patent Number: 6,059,913
[45] Date of Patent: May 9, 2000

[54] METHOD FOR PRODUCING TRANSDERMAL PATCHES (TTS)

[75] Inventors: Bodo Asmussen, Bendorf-Sayn; Thomas Hille, Neuwied; Klaus Schumann, Neuwied; Peter Steinborn, Neuwied, all of Germany

[73] Assignee: LTS Lohmann Therapie-Systeme GmbH, Neuwied, Germany

[21] Appl. No.: 09/091,696

[22] PCT Filed: Dec. 4, 1996

[86] PCT No.: PCT/EP96/05410

§ 371 Date: Oct. 30, 1998

§ 102(e) Date: Oct. 30, 1998

[87] PCT Pub. No.: WO97/22315

PCT Pub. Date: Jun. 26, 1997

[30] Foreign Application Priority Data

Dec. 20, 1995 [DE] Germany ............................ 195 47 691

[51] Int. Cl.[7] ............................ B44C 1/165; B32B 4/00; B23B 31/00; A61L 13/00; A61F 13/00
[52] U.S. Cl. ................... 156/230; 156/238; 156/247; 156/248; 156/289; 156/344; 427/2.31; 424/449
[58] Field of Search ...................... 156/230, 234, 156/235, 239, 247, 248, 249, 289, 344; 427/2.31; 424/449

[56] References Cited

U.S. PATENT DOCUMENTS 5,492,590  2/1996  Sakai .................................... 156/344
5,681,413  10/1997  Hille et al. ............................ 156/238

*Primary Examiner*—Richard Crispino
*Assistant Examiner*—J. A. Lorengo
*Attorney, Agent, or Firm*—Ann W. Speckman; Jim Klaniecki

[57] ABSTRACT

A process for the continuous production of transdermal therapeutic patches, wherein a laminate of an auxiliary layer (3) siliconized at least on one side, an active substance-containing, pressure-sensitive adhesive layer (4), and a supporting layer (9) is prepared as a strip-shaped web (1) first, and the active substance-containing sections (4') obtained by punching said layers (3) and (4) across the web direction are intermittently transferred onto a second web (2), the punching procedure taking place in the rest phase between the cycles and the transfer procedure onto the second web (2) being carried out preferably at equal distances by means of a transfer device (11, 12), is characterized by the fact that the supporting layer (9) is stripped from the active substance-containing sections (4') during the transfer first, and that then the sections (3') of the auxiliary layer are removed with the aid of a process layer (5) which has been rendered pressure-sensitive adhesive.

4 Claims, 2 Drawing Sheets

METHOD FOR PRODUCING TRANSDERMAL PATCHES (TTS)

The present invention relates to a process for the production of transdermal therapeutic patches (TTS) according to the introductory part of claim 1.

A process for continuously producing and filling patch packages with an active substance to be administered transdermally is known from DE-PS 32 04 582. The active substance is applied on a supporting film in portions and at certain distances, covered by metallic sealing film sections, and then, using an interlayer film, covered with an elastic adhesive film which is adherent on one side that is directed towards said interlayer film; after that the active substance portions, with their surrounding film layers, are punched to the desired size. This process involves a relatively heavy technical expenditure and relatively large amounts of useless material.

A process for the continuous production of transdermal therapeutic patches is also known. First, a laminate is produced by coating an intermediate carrier film with a flowable, active substance-containing preparation, this is then cut to strips of predetermined width, and, in further process stages, these are cut into active substance-containing sections of a defined length; these are applied at given distances on a protective film which covers them on all sides; finally, they are subdivided into single patches by cutting the protective film across the strip direction between the active substance-containing sections. Although this process most advantageously achieves the object of substantially preventing or minimizing active substance losses, it is relatively complicated because of the numerous process stages.

Another process is described in DE-OS 41 10 027. It describes a process for the continuous production of transdermal therapeutic patches having a backing layer, a pressure-sensitive adhesive active substance reservoir layer, and a removable protective layer; during manufacture active substance loss is minimized. In this process, the pressure-sensitive adhesive active substance reservoir is transferred onto the protective layer, which is formed in a later stage, in the form of a laminate consisting of an active substance-containing pressure-sensitive adhesive layer and a polymer film by means of a dispenser edge. However, the disadvantage of this process is that the final product, after removal of the protective film, has two polymer films in any case, and the resulting rigidity of the whole TTS can in some cases cause an unsatisfactory wearing comfort.

It is accordingly the object of the present invention to transfer single, active substance-containing sections at a high rate, high precision, and without active substance loss from a first web at predetermined distances one after the other onto a second web, which preferably projects the sections on all sides, in a technically simple and reliable manner; in this connection, it must be avoided that the wearing comfort of the final product is impaired by a polymer film lying within the TTS.

This object is achieved according to the present invention with a process according to claim 1. In view of the fact that it has been regarded as a standing rule for technical action among experts that pressure-sensitive adhesive films can only be transferred in the form of laminates with rigid sheet materials, this solution is all the more remarkable.

DE-OS 41 10 027, DE-OS 15 11 873, DE-PS 25 55 910, DE-OS 32 33 546, DE-PS 36 18 542, and DE 42 32 279 describe transfer processes; however, the possibility of removing the process film during the transfer of the self-adhesive laminate is not mentioned therein.

When the patch according to the present invention is produced, a more or less great number of layers may be provided according to the requirements, i.e., depending on the intended use of the patch, each individual layer consisting of suitable materials, such as metal, preferably aluminum, polymers, or textile fabrics. Depending on their respective purpose the individual layers may be self-adhesive or also repellent to adhesives, permeable or also impermeable to active substances, flexible or inflexible.

Active substance-containing sections may have different forms, for example, a rectangular, square, oval, or circular form. With respect to avoiding active substance losses, however, a rectangular or square form is preferable.

Possible additives depending on the polymers used for the production of the active substance-containing layer and the active substance include, for example, plasticizers, tackifiers, stabilizers, carriers, diffusion and penetration regulating additives, or fillers. Suitable physiologically acceptable substances are known to the skilled artisan. The self-tackiness of the active substance-containing layer is intended to ensure permanent contact to the skin.

A protective layer of the active substance-containing layer, which is to be removed prior to application, may consist, for example, of the same materials as those used for the production of the backing layer. However, these must be rendered removable, for example, by means of a silicone treatment. Other removable protective layers include, for example, tetrafluoroethylene, treated paper, cellophane, polyvinyl chloride, and the like.

The process and auxiliary layers may be made of the same materials.

The pressure-sensitive adhesive layers may be made, for example, of a polymer matrix having a base polymer and optional conventional additives. Suitable materials include, for example, silicones, rubber, rubber-like synthetic homo-, co-, or block polymers, polyacrylates and their copolymers, and also esters of hydrogenated colophony.

Basically, any polymer is suitable which is used in the production of pressure-sensitive adhesives and is physiologically acceptable. Particularly preferred ones are those which as a block copolymer based on styrene and 1,3-diene, polyisobutylene, or polymers and copolymers, consist of acrylate and/or methacrylate. Linear styrene-isoprene-styrene block copolymers are preferably used among the block copolymers based on styrene and 1,3-diene.

Substances that are applied on the skin without or with absorption mediators and which cause a local or systemic action are used as active substances.

Substances having a local effect include, for example, antiperspirants, fungicides, bactericides, and bacteriostatics.

Substances having a systemic effect include, for example, antibiotics, hormones, antipyretics, antidiabetic agents, coronary vasodilators, cardio-active glycosides, spasmolytics, hypotensives, psychotropics, migraine analgesics, corticoids, analgesics, contraceptives, antirheumatics, cholinergics or anticholinergics, symphaticomimetics or symphaticolytics, vasodilators, anticoagulants, or antiarrythmics. As a matter of fact, there are other suitable active substances.

Figure 1:
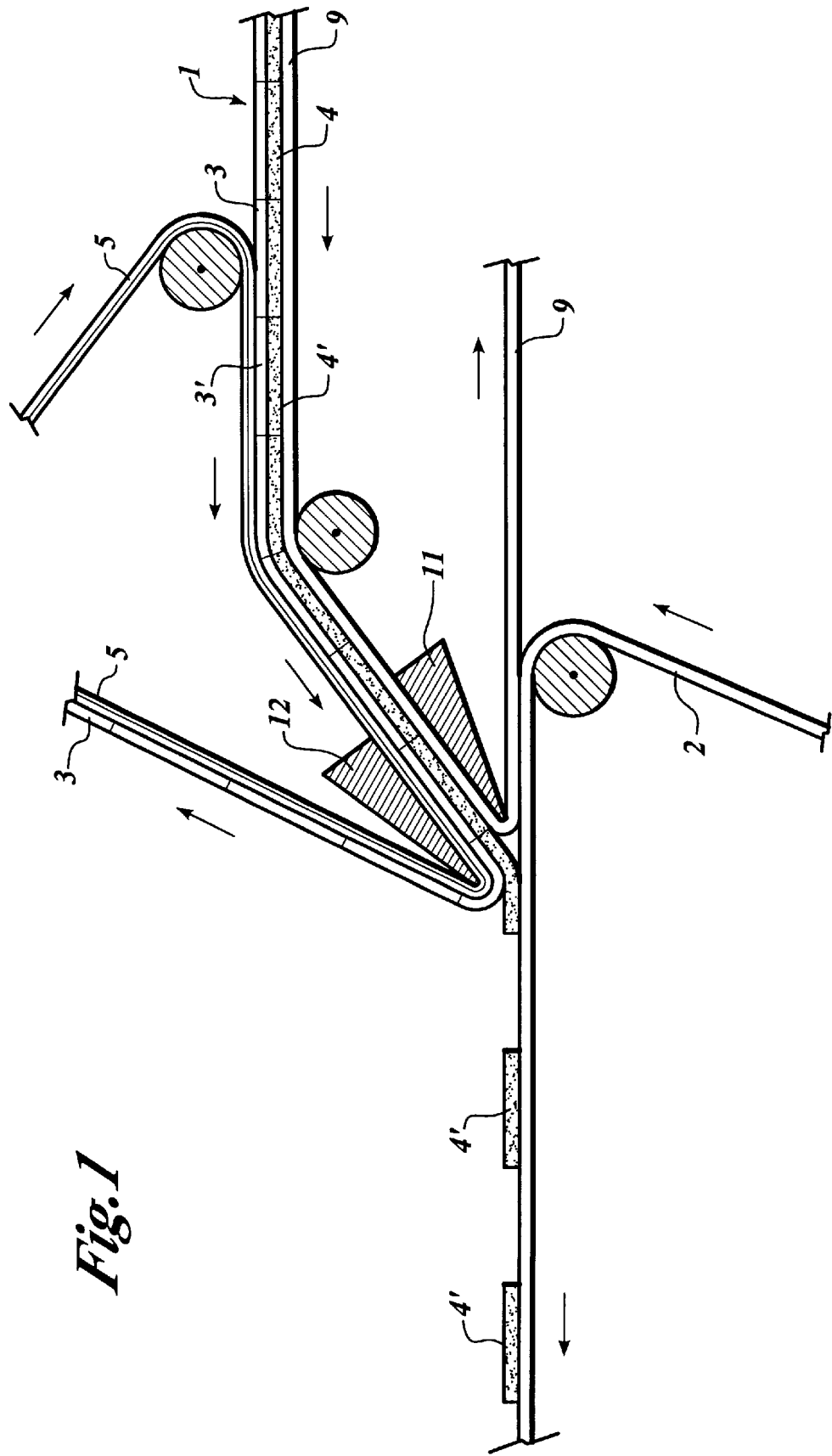
FIG. 1 is a schematic illustration of an apparatus for the production of transdermal therapeutic patches in accordance with the present invention.

The present invention is shown in the drawings by way of embodiment examples, in the following it will be exemplified with reference to the drawings:

In FIG. 1, (1) is the first web-shaped laminate or the first web; from the top to the bottom it consists of an auxiliary layer made of film (3) siliconized at least on one side, an active substance-containing, pressure-sensitive adhesive layer (4), and a supporting layer (9) (siliconized at least on one side).

Using a cutting device, the film (3) and the active substance-containing layer (4) are separated with a straight cut perpendicular to the web direction so that, for example, square sections (3',4') result. The siliconized supporting film (9) is not cut. With the help of a gripper feed system, which can also be a roller feed system or the like, the first web (1) is transported from the right to the left. during the movement phase and then secured by means of a hold-down device. Immediately after cutting the layers (3) and. (4), the laminate (5) which consists of a pressure-sensitive adhesive process film is laminated to the web-shaped laminate (1) on the side of layer (3). At the first dispensing edge (11) of the transfer device, the active substance-containing, pressure-sensitive adhesive sections (4') of layer (4) are released from the carrier film (9).

Via a second dispensing edge (12), the sections (3') of layer (3) are stripped from the active substance-containing, pressure-sensitive adhesive sections (4'). After that, sections (4') adhere to the second web (2).

The directions of movement of all the webs are indicated by arrows.

Figure 2:
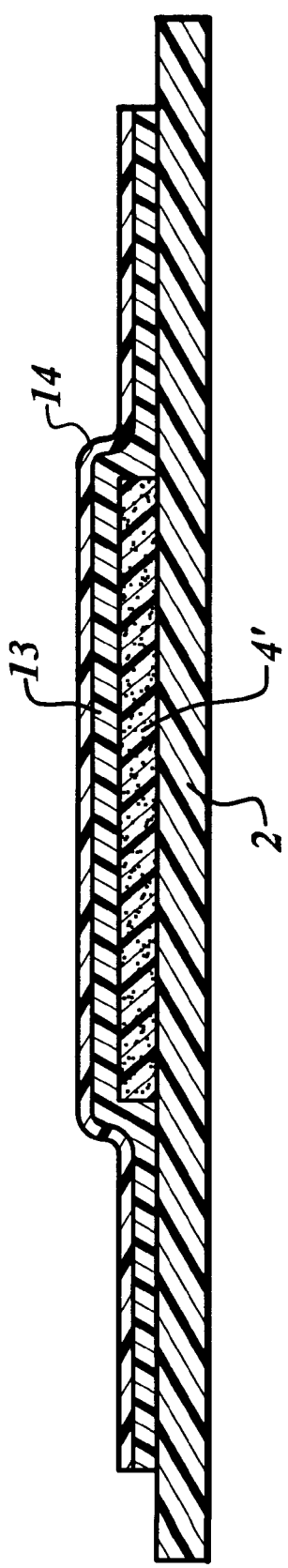
FIG. 2 is a cross-section of a transdermal therapeutic patch carried on a film having a laminate consisting of a pressure-sensitive adhesive layer and film layer disposed there over prior to cutting in accordance with the present invention.

A laminate consisting of a pressure-sensitive adhesive layer (13) which is free of active substance and a film (14) which is impermeable to active substances (backing layer) is laminated over the whole surface of the second web (2) (FIG. 2). The individual patches are punched out by cutting layers (13) and (14) but not (2).

The lattice-like scrap of layers (13) and (14) which results between the sections (4') is removed. The individual patches are obtained by cross cutting (2) (FIG. 2).

With a thickness of 100 g/m$^2$, for example, the active substance-containing, pressure-sensitive adhesive layer (4) may comprise 57% solution polyacrylate, 25% plasticizer, 10% polymethacrylate, and 8% physostigmine. With a web width of 35 mm, square patch formats (4') of the size 35×35 mm may be obtained. In this case, the second web (2) has a width of about 55 mm and may be formed of a polyester film (PET) siliconized on both sides.

What is claimed is:

1. A process for the continuous production of transdermal therapeutic patches, wherein a laminate of an auxiliary layer (3) siliconized at least on one side, an active substance-containing, pressure-sensitive adhesive layer (4), and a supporting layer (9) is prepared as a strip-shaped web (1) first, and the active substance-containing sections (4') obtained by punching said layers (3) and (4) across the web direction are intermittently transferred on a second web (2), the punching procedure taking place in the rest phase between the cycles and the transfer procedure onto the second web (2) being carried out preferably at equal distances by means of a transfer device (11, 12), characterized in that the supporting layer (9) is stripped from the active substance-containing sections (4') during the transfer first, and that then the sections (3') of the auxiliary layer are removed with the aid of a process layer (5) which has been rendered pressure-sensitive adhesive.

2. The process according to claim 1 characterized in that the strip-shaped web (1) and the second web (2) are intermittently forwarded at differing movement and rest phases, and/or differing step lengths, and/or differing rates.

3. The process according to claim 1 characterized in that the transfer devices are moved to-and-fro in web direction during the transfer of the active substance-containing sections (4').

4. The process according to claim 1, characterized in that the supporting layer is continuously stripped from the active substance-containing sections during the transfer and subsequently, the sections of the auxiliary layer are continuously removed with the aid of a process layer comprising a pressure-sensitive adhesive.

* * * * *